United States Patent [19]

Mahar

[11] Patent Number: 5,877,247

[45] Date of Patent: Mar. 2, 1999

[54] STABLE MAGNESIUM HYDROXIDE SLURRIES

[76] Inventor: Robert Crouse Mahar, 1335 Fennel Rd., Pennsburg, Pa. 18073

[21] Appl. No.: 956,529

[22] Filed: Oct. 5, 1992

[51] Int. Cl.$^6$ .............................. C08L 33/02; C01F 5/14
[52] U.S. Cl. ......................... 524/433; 524/436; 524/556; 106/471
[58] Field of Search .................................. 524/433, 436, 524/556

[56] References Cited

U.S. PATENT DOCUMENTS

| 4,046,707 | 9/1977 | Smith et al. . | |
|---|---|---|---|
| 4,230,610 | 10/1980 | Falcione et al. . | |
| 4,375,526 | 3/1983 | Zupanovich et al. . | |
| 4,430,248 | 2/1984 | Rey . | |
| 4,450,013 | 5/1984 | Hirsch et al. ............................ | 524/436 |
| 4,588,649 | 5/1986 | Kriz et al. ................................ | 524/446 |
| 4,681,686 | 7/1987 | Richardson et al. . | |
| 4,743,396 | 5/1988 | Fong et al. . | |
| 4,818,783 | 4/1989 | Shioji et al. ............................ | 524/425 |

FOREIGN PATENT DOCUMENTS 61-56168  12/1986  Japan .

*Primary Examiner*—Andrew E. C. Merriam
*Attorney, Agent, or Firm*—Ronald S. Hermenau; David T. Banchik

[57] ABSTRACT

A stabilized aqueous slurry of magnesium hydroxide and a method for preparing the same are provided. The method involves an aqueous magnesium hydroxide slurry prepared with a combination of (a) one or more polymeric dispersants and (b) one or more water-soluble alkali metal salts. Slurries prepared according to the invention are less susceptible to increases in viscosity upon standing and remain flowable after several days.

20 Claims, No Drawings

STABLE MAGNESIUM HYDROXIDE SLURRIES

FIELD OF THE INVENTION

This invention relates to a method of preparing stable magnesium hydroxide slurries. More particularly, this invention relates to a method of preparing stable magnesium hydroxide slurries using a combination of (a) one or more polymeric dispersants and (b) one or more water-soluble alkali metal salts. Slurries prepared according to the invention are less susceptible to increases in viscosity upon standing and remain flowable after several days.

BACKGROUND OF THE INVENTION

Magnesium hydroxide is used in large quantities in various applications including toothpaste additives and as an acid neutralizer. Magnesium hydroxide [$Mg(OH)_2$] is also the precursor in the manufacture of magnesium oxide (MgO) which is used in antacid formulations and as a pigment in the paper industry. It is desirable to be able to ship and store magnesium hydroxide as a high solids aqueous slurry. However, these slurries are fairly unstable and form either gels or hard-pack sediment upon standing, thereby rendering the slurries difficult to use and potentially damaging to piping, pumps, and other slurry handling mechanical equipment.

Magnesium hydroxide and magnesium oxide slurry stability has been the subject of extensive research and has been a long standing problem for the magnesium hydroxide industry. The art has addressed the problem by focusing on methods of reducing the viscosity of high solids magnesium hydroxide slurries. U.S. Pat. No. 4,230,610 teaches a method of reducing the viscosity of magnesium oxide slurries by using 0.1 to 5.0 percent by weight of poly(acrylic acid) neutralized to a pH of from about 8.0 to about 12.0. U.S. Pat. No. 4,375,526 teaches a method of reducing the viscosity and enhancing the stability of magnesium hydroxide slurries by using anionic polymers and copolymers. U.S. Pat. No. 4,430,248 teaches a method of reducing the viscosity of magnesium hydroxide slurries by using cationic polymers and copolymers.

Those approaches are somewhat effective in reducing the viscosity of magnesium oxide and magnesium hydroxide slurries but I have found that these approaches are not satisfactory for maintaining the stability of the slurries over an extended period of time.

It is an object of this invention to provide a method of preparing stable aqueous slurries of magnesium hydroxide.

SUMMARY OF THE INVENTION

This invention is directed to a method of preparing stable aqueous magnesium hydroxide slurries by using a combination of (a) one or more polymeric dispersants and (b) one or more water-soluble alkali metal salts.

DETAILED DESCRIPTION OF THE INVENTION

The one or more polymeric dispersants which are suitable for the present invention are anionic polymeric dispersants which are effective at dispersing aqueous slurries of magnesium hydroxide. Anionic polymers include, for example, homopolymers, copolymers and terpolymers having carboxylic acid, sulphonic acid or phosphonic acid functionalities. Monomers which impart acid functionality include, for example, acrylic acid, methacrylic acid, crotonic acid, maleic acid, maleic anhydride, itaconic acid, mesaconic acid, fumaric acid, citraconic acid, vinylacetic acid, acryloxypropionic acid, vinylsulfonic acid, styrenesulfonic acid, 2-acrylamido-2-methylpropanesulfic acid, allylsulfonic acid, allylphosphonic acid, vinylphosphonic acid, and vinylsulfonic acid.

Anionic polymeric dispersants may also be formed, in part, from monomers which do not contribute to the carboxylic, sulphonic or phosphonic acid functionality of the polymer. Monomers which do not contribute to the carboxylic, sulphonic or phosphonic acid functionality of the polymer include, for example: alkyl esters of acrylic and methacrylic acid such as methyl, ethyl and butyl acrylate and methyl, butyl and isobutyl methacrylate; hydroxyalkyl esters of acrylic and methacrylic acids, such as hydroxyethyl and hydroxypropyl acrylate and methacrylate; acrylamide; methacrylamide; N-tertiarybutylacrylamide; N-methylacrylamide; N,N-dimethylacrylamide; dimethylaminoethyl acrylate; dimethylaminoethyl methacrylate; N-vinylpyrrolidone; N-vinylformamide; phosphoethyl methacrylate; allyl and methallyl alcohols, esters and ethers; acrylonitrile; vinyl acetate; and styrene. Monomers which do not contribute to the carboxylic, sulphonic or phosphonic acid functionality of the polymer may be present in the polymer at levels up to the point where the polymer is no longer water-soluble. Generally, monomers which do not contribute to the carboxylic, sulphonic or phosphonic acid functionality of the polymer will be present in the polymers at a level of below 50 percent by weight, preferably below 30 percent by weight.

Anionic polymeric dispersants can be used in their acid forms, or they can be used in a partially or fully neutralized form. The anionic polymeric dispersants can be neutralized with any suitable base, such as alkali metal or ammonium hydroxides. Preferably, the anionic polymeric dispersant is fully neutralized with sodium hydroxide. The polymeric dispersants generally have a weight average molecular weight ($M_w$) of from about 1,000 to about 50,000 as measured by aqueous gel permeation chromatography (gpc). Where "$M_w$" appears, it refers to the $M_w$ as measured by aqueous gpc.

The method of preparing anionic polymeric dispersants is well known to those skilled in the art. The anionic polymers can be prepared by solvent, aqueous, or solvent-free processes. The art of preparing anionic polymeric dispersants has also employed various methods of controlling the molecular weight of polymers to produce polymers having $M_w$ below about 50,000. These methods include the use of chain transfer agents, metal activators and increased levels of initiators.

In one embodiment of the present invention, it has been found to be beneficial to use as the one or more anionic polymeric dispersants, homopolymers, copolymers, or terpolymers made using hypophosphites (such as sodium hypophosphite or ammonium hypophosphite) as a chain transfer agent. Suitable polymeric dispersants prepared using sodium hypophosphite as a chain transfer agent are taught, for example, in U.S. Pat. Nos. 4,046,707 and 4,681,686 incorporated by reference herein. Particularly preferred polymeric dispersants prepared using sodium hypophosphite as a chain transfer agent are, for example, homopolymers of acrylic acid and salts thereof and copolymers of acrylic acid and maleic anhydride or maleic acid and salts thereof.

The water-soluble alkali metal salts which are suitable for the present invention include alkali metal hydroxides, alkali metal halides, alkali metal carbonates, alkali metal sulfates, alkali metal nitrates, alkali metal phosphates, and alkali metal silicates. Preferred inorganic alkali metal salts are sodium hydroxide, potassium hydroxide, sodium carbonate, potassium carbonate, sodium chloride, potassium chloride, and sodium sulfate. Suitable organic alkali metal salts are the water-soluble alkali metal salts of $C_1$–$C_6$ carboxylic acids and $C_2$–$C_{10}$ polycarboxylic acids including alkali metal formates, alkali metal acetates, alkali metal propionates, alkali metal butyrates, alkali metal oxalates, alkali metal malonates, alkali metal succinates, alkali metal glutarates, alkali metal adipates, alkali metal fumarates, alkali metal maleates, alkali metal phthalates, alkali metal aconiticates, alkali metal tartarates, alkali metal ketoglutarates, and alkali metal citrates. A preferred organic alkali metal salt is sodium citrate.

The slurries of this invention contain from about 30 to about 70 percent, and preferably from about 40 to about 60 percent by weight of magnesium hydroxide.

The one or more water-soluble alkali metal salts are added to the magnesium hydroxide slurry to a level of from about 0.2 to about 20 percent by weight based on the weight of magnesium hydroxide, and preferably from about 0.3 to about 10 percent by weight based on the weight of magnesium hydroxide. The addition of one or more water-soluble alkali metal salts to the magnesium hydroxide slurry may affect the viscosity of the slurry. It is desirable to add the one or more water-soluble alkali metal salts to provide an initial slurry viscosity of between about 100 and about 4,000, preferably between about 300 and about 3,000. It is also preferable that the one or more water-soluble alkali metal salts are added to the magnesium hydroxide slurry to a level which provides a weight ratio of alkali metal salt to polymeric dispersant of from about 10:1 to about 1:10, and most preferably from about 2:1 to about 1:2.

The one or more anionic polymeric dispersants are added to the magnesium hydroxide slurry to a level of from about 0.2 to about 20 percent by weight, and preferably from about 0.3 to about 10 percent by weight based on the weight of magnesium hydroxide. It is particularly preferred to add the one or more anionic polymeric dispersants to the magnesium hydroxide slurry to a level which is within about 0.1 percent by weight (based on the weight of magnesium hydroxide) of the minimum viscosity dispersant dosage ("MVDD"). The minimum viscosity dispersant dosage is the level of dispersant beyond which there is no appreciable decrease in slurry viscosity. The actual MVDD will vary depending upon the type of polymeric dispersant and the solids level of the slurry. The minimum viscosity dispersant dosage for a given slurry can readily be determined by monitoring the viscosity of the slurry as the level of dispersant is increased.

Determination of MVDD for a 50 Percent by Weight Slurry of $Mg(OH)_2$

The MVDD of the sodium salt of a polymer of 95 percent by weight acrylic acid and 5 percent by weight ethyl acrylate having $M_w$ 2,800 made using sodium metabisulfite as a chain transfer agent (referred to hereinafter as "Polymer A") was determined in a 50 percent by weight aqueous slurry of magnesium hydroxide in the following manner:

To 225.0 grams of deionized water was added 225.0 grams of dried magnesium hydroxide. This mixture was stirred with a spatula for one minute. The pH of the mixture was 9.7. The polymeric dispersant was added as an aqueous solution of 45 percent by weight polymer solids to the aqueous mixture. This mixture was stirred with a spatula until it was completely mixed. The viscosity of the slurry was then measured at 23° C. using a Brookfield viscometer, model RVT, spindle #2 at 20 revolutions per minute (rpm). Additional polymeric dispersant was added to the mixture and the viscosity was measured in the same manner as before. The data appear in Table I, below. The polymer level reported in Table I is the weight percent of Polymer A solids based on the weight of magnesium hydroxide.

TABLE I

MVDD of Polymer A in a 50 Percent By Weight Slurry of $Mg(OH)_2$

| Polymer A Level | Viscosity (centipoises) |
| --- | --- |
| 0.44 | 1450 |
| 0.49 | 665 |
| 0.54 | 264 |
| 0.57 | 120 |
| 0.59 | 60 |
| 0.62 | 42 |
| 0.64 | 30 |
| 0.67 | 30 |
| 0.70 | 30 |

The data in Table I show that the minimum viscosity dispersant dosage for the 50 percent by weight magnesium hydroxide slurry using the polymeric dispersant described above is 0.64 percent by weight based on the weight of magnesium hydroxide; at dispersant levels beyond 0.64 percent by weight, no decrease in viscosity was observed.

Stability Test of Anionic Polymeric Dispersant

Magnesium hydroxide slurries, to which only a polymeric dispersant has been added, were tested for stability over time. This is shown in Table II, below. Two magnesium hydroxide slurries were prepared with a polymeric anionic dispersant and the viscosity was measured as a function of time. The magnesium hydroxide slurries were made in the following way: the anionic polymeric dispersant was added to deionized water and diluted with additional deionized water to 225 grams. The anionic polymeric dispersant, designated Polymer B in the Tables below, was a 42 percent by weight aqueous solution of the sodium salt of a 3,500 $M_w$ poly(acrylic acid) made using sodium hypophosphite as a chain transfer agent. This mixture was stirred with a spatula until it was completely mixed. Then, 225.0 grams of dried magnesium hydroxide was added to the mixture and the mixture was stirred at high speed on a Waring blender for five minutes. The viscosity of the slurry was then measured at 23° C. using a Brookfield viscometer, model RVT, spindle #2 at 20 rpm. The polymer level reported in Table II is the weight percent of polymer solids based on the weight of magnesium hydroxide. The results appear in Table II, below.

TABLE II

| Polymer B Level | Time (minutes) | Viscosity (centipoises) |
| --- | --- | --- |
| 0.65 | 0 | 380 |
|  | 4 | 940 |
|  | 110 | 9,040 |
| 0.70 | 0 | 60 |
|  | 4 | 268 |

The data in Table II show that the magnesium hydroxide slurries to which only a polymeric dispersant has been added, are not stable over time. Dispersants do act to lower the viscosity of the magnesium hydroxide slurry, but the lower viscosity is not maintained.

Stability Test of Anionic Polymeric Dispersant and Alkali Metal Salt

By contrast, magnesium hydroxide slurries prepared in accordance with the present invention exhibit stability over time. The magnesium hydroxide slurry appearing in Table III, below, was made in the same manner as the slurries appearing in Table II, above, except that 0.6 percent by weight based on the weight of magnesium hydroxide was $Na_2CO_3$.

TABLE III

| Polymer B Level | $Na_2CO_3$ Level | Time (minutes) | Viscosity (centpoises) |
|---|---|---|---|
| 0.6 | 0.6 | 0 | 1600 |
| | | 4 | 1119 |
| | | 110 | 970 |

The data appearing in Table III show that the magnesium hydroxide slurry made with a combination of an anionic polymeric dispersant and a water-soluble alkali metal salt is stable over time. The slurry viscosity did not increase in the course of 110 minutes. The slurry appearing in Table III was allowed to stand for four days. After four days, the slurry formed a loose gel. When this loose gel was disrupted with very slight agitation by a spatula, the slurry flowed from the inverted container without exhibiting hard-pack formation or gellation.

The magnesium hydroxide slurries appearing in Table IV, below, were made in the following way: the anionic polymeric dispersant (Polymer B unless indicated otherwise) and the water-soluble alkali metal salt were added to deionized water and diluted with additional deionized water to 225.0 grams. This mixture was stirred with a spatula until it was completely mixed. Then, 225.0 grams of dried magnesium hydroxide was added to the mixture and the mixture was stirred at high speed on a Waring blender for five minutes. The viscosity of the slurry was then measured at 23° C. using a Brookfield viscometer, model RVT, spindle #2 at 20 rpm. The polymer level reported in Table IV is the weight percent of polymer solids based on the weight of magnesium hydroxide. The salt level reported in Table IV is the weight percent of the alkali metal salt based on the weight of magnesium hydroxide. The viscosity results and observations on the stability of the slurry after standing for three days at room temperature appear in Table IV, below.

TABLE IV

| Polymer Level | Salt Level | Salt Type | Initial Viscosity (centipoises) | 3 Day Stability |
|---|---|---|---|---|
| none | 0.6 | $Na_2CO_3$ | a | — |
| none | 0.6 | $Na_2CO_3$ | 2,350 | d |
| none | 0.6 | sodium citrate | a | — |
| 0.6 | none | — | 7,000 | d |
| 0.6[1] | none | — | 7,000 | d |
| 0.3 | 0.3 | sodium citrate | 9,950 | d |
| 0.4 | 0.4 | sodium citrate | 3,820 | b |
| 0.5 | 0.5 | sodium citrate | 740 | c |
| 0.6 | 0.6 | sodium citrate | 40 | e |
| 0.7 | 0.6 | $Na_2CO_3$ | 1,250 | b |
| 0.6 | 0.6 | $Na_2CO_3$ | 1,600 | c |
| 0.5 | 0.6 | $Na_2CO_3$ | 2,800 | c |
| 0.4 | 0.6 | $Na_2CO_3$ | 6,000 | b |
| 0.6 | 0.7 | $Na_2CO_3$ | 2,420 | b |
| 0.6 | 0.5 | $Na_2CO_3$ | 3,270 | b |
| 0.6 | 0.6 | $Na_2CO_3$ | 1,270 | b |
| 0.6 | 0.6 | $Na_2CO_3$ | 2,100 | b |
| 0.6[1] | 0.6 | $Na_2CO_3$ | 3,250 | c |
| 0.7[2] | 0.6 | $Na_2CO_3$ | 1,670 | c |

[1]Polymer A
[2]sodium salt of poly(acrylic acid) having $M_w$ 4,500 made using sodium metabisulfite as a chain transfer agent
a - heavy paste, viscosity too high to be considered a stable slurry
b - after very slight agitation (1 revolution) with a spatula, slurry flowed from the container
c - after mild agitation (2 to 4 revolutions) with a spatula, slurry flowed from the container
d - slurry did not flow
e - initial slurry viscosity was too thin to maintain stability; 30 percent by volume hard pack formation in three days The data appearing in Table IV show that magnesium hydroxide slurries made without an anionic polymeric dispersant, or without a water-soluble alkali metal salt, do not flow from an inverted container after three days. The data also show that stable magnesium hydroxide slurries can be prepared according to the present invention with anionic polymeric dispersants having a variety of compositions and molecular weights. The data also show that stable magnesium hydroxide slurries can be prepared according to the present invention with various alkali metal salts.

The magnesium hydroxide slurries appearing in Table V, below, were made in the same manner as the slurries appearing in Table IV. The slurries were maintained at a slightly elevated temperature, 27° C. After one hour and after 9 days, the viscosity of the slurry was then measured at 23° C. using a Brookfield viscometer, model RVT, spindle #2 at 100 rpm. The polymer level reported in Table V is the weight percent of polymer solids based on the weight of magnesium hydroxide. The salt level reported in Table V is the weight percent of the alkali metal salt based on the weight of magnesium hydroxide. After 14 days at 27° C., the container holding the slurry was inverted. The percent by weight of the slurry which flowed from the container and other observations are reported in Table V in the column entitled "Stability" under the heading "No Mixing." The slurry was then gently stirred (2 to 4 revolutions) with a spatula; the percent by weight of the original slurry which flowed from the container and other observations are reported in Table V in the column entitled "Stability" under the heading "Mild Mixing." The slurry was then vigorously stirred (8 or 10 revolutions) with a spatula; the percent by weight of the original slurry which flowed from the container and other observations are reported in Table V in the column entitled "Stability" under the heading "Strong Mixing." The data reported in Table V as 100% does not include the weight of the residual slurry coating the surface of the container.

TABLE V

| Polymer Type | Polymer Level | Salt Level | Salt Type | Viscosity (centipoises) 1 hour | Viscosity (centipoises) 9 days | Stability (14 days at 27° C.) No Mixing | Stability (14 days at 27° C.) Mild Mixing | Stability (14 days at 27° C.) Strong Mixing |
|---|---|---|---|---|---|---|---|---|
| none | none | none | none | 8,600 | 6,400 | No flow | No flow | No flow |
| Polymer B | 0.6 | none | none | 1,910 | 2,910 | No flow | No flow | Slight flow |
| Polymer B | 0.9 | none | none | 350 | 568[b] | No flow | No flow | No flow |
| Polymer B | 1.2 | none | none | 36 | b | 48% | 64% | b |
| none | none | 0.6 | $Na_2CO_3$ | 6,090 | 4,960 | No flow | No flow | No flow |
| none | none | 1.2 | $Na_2CO_3$ | 4,510 | 3,470 | No flow | No flow | No flow |
| Polymer B | 0.5 | 0.6 | $Na_2CO_3$ | 554 | 422 | No flow | 100% flow | — |
| Polymer B | 0.6 | 0.6 | $Na_2CO_3$ | 370 | 378 | No flow | 100% flow | — |
| Polymer A | 0.6 | 0.6 | $Na_2CO_3$ | 466 | 364 | 53% | 100% flow | — |
| Polymer C[1] | 0.6 | 0.6 | $Na_2CO_3$ | 364 | 309 | 56% | 100% flow | — |
| Polymer D[2] | 0.6 | 0.6 | $Na_2CO_3$ | 679 | 730 | No flow | 100% flow | — |
| Polymer E[3] | 0.6 | 0.6 | $Na_2CO_3$ | 804 | 914 | No flow | 38% | 100% flow |
| Polymer F[4] | 0.6 | 0.6 | $Na_2CO_3$ | 356 | 450 | No flow | 11% | 78% |
| Polymer G[5] | 0.6 | 0.6 | $Na_2CO_3$ | 486 | 596 | No flow | No flow | 78% |
| Polymer H[6] | 0.6 | 0.6 | $Na_2CO_3$ | 610 | 410 | 22% | 100% flow | — |
| Polymer B | 0.6 | 0.45[a] | NaOH | 1,240 | 1,010 | 10% | 100% flow | — |
| Polymer B | 0.6 | 0.40[a] | NaCl | 1,770 | 1,980 | Syneresis | 27% | 69% |
| Polymer B | 0.6 | 0.80a | $Na_2SO_4$ | 1,620 | 1,920 | No flow | 33% | 67% |

[1]similar to Polymer B except $M_w$ = 2,800
[2]similar to Polymer B except $M_w$ = 4,700
[3]similar to Polymer B except $M_w$ = 7,700
[4]similar to Polymer B except $M_w$ = 12,400
[5]similar to Polymer B except $M_2$ = 18,400
[6]sodium salt of poly(acrylic acid) having $M_w$ 2,000 made using sodium metabisulfite as a chain transfer agent
[a]the salt was added at a level to provide an equivalent level of sodium as 0.6 percent by weight of $Na_2CO_3$
[b]initial viscosity too low for stable slurry formation; significant hard pack formation; could not be mixed The data appearing in Table V show that magnesium hydroxide slurries made without an anionic polymeric dispersant, or without an alkali metal salt, do not flow from an inverted container after 14 days. The data also show that stable magnesium hydroxide slurries can be prepared according to the present invention with anionic polymeric dispersants having a variety of compositions and molecular weights. The data also show that stable magnesium hydroxide slurries can be prepared according to the present invention with a variety of alkali metal salts. The data also show that the viscosity of the slurries prepared according to the present invention are fairly constant after nine days.

I claim:

1. A method of preparing a stable aqueous slurry of magnesium hydroxide comprising:
   (a) forming an aqueous mixture of
      (i) from about 30 to about 70 percent by weight magnesium hydroxide;
      (ii) from about 0.2 to about 20 percent by weight based on the weight of magnesium hydroxide of one or more polymeric anionic dispersants and salts thereof; and
      (iii) from about 0.2 to about 20 percent by weight based on the weight of magnesium hydroxide of one or more water-soluble alkali metal salts selected from the group consisting of alkali metal hydroxides alkali metal halides, alkali metal carbonates, alkali metal sulfates, alkali metal nitrates, alkali metal silicates and alkali metal salts of $C_2$–$C_{10}$ polycarboxylic acids; and
   (b) agitating the mixture to suspend the magnesium hydroxide.

2. The method of claim 1, wherein magnesium hydroxide is from about 40 to about 60 percent by weight of the aqueous mixture.

3. The method of claim 1, wherein the one or more polymeric anionic dispersants are from about 0.3 to about 10 percent by weight based on the weight of magnesium hydroxide.

4. The method of claim 1, wherein the one or more water-soluble alkali metal salts are from about 0.3 to about 10 percent by weight based on the weight of magnesium hydroxide.

5. The method of claim 1, wherein magnesium hydroxide is from about 40 to about 60 percent by weight of the aqueous mixture, the one or more water-soluble alkali metal salts are from about 0.3 to about 10 percent by weight based on the weight of magnesium hydroxide, and the one or more polymeric anionic dispersants are from about 0.3 to about 10 percent by weight based on the weight of magnesium hydroxide.

6. The method of claim 1, wherein the one or more water-soluble alkali metal salts are selected from the group consisting of sodium hydroxide, potassium hydroxide, sodium carbonate, potassium carbonate, sodium chloride, potassium chloride and sodium sulfate.

7. The method of claim 1, wherein the one or more water-soluble alkali metal salts is sodium carbonate.

8. The method of claim 1, wherein the one or more water-soluble alkali metal salts are alkali metal salts of $C_2$–$C_{10}$ polycarboxylic acids selected from the group consisting of alkali metal oxalates, alkali metal malonates, alkali metal succinates, alkali metal glutarates, alkali metal adipates, alkali metal fumarates, alkali metal maleates, alkali metal phthalates, alkali metal aconiticates, alkali metal tartarates, alkali metal ketoglutarates and alkali metal citrates.

9. The method of claim 1, wherein the one or more water-soluble alkali metal salts is sodium citrate.

10. The method of claim 1, wherein the one or more water-soluble alkali metal salts are alkali metal salts of $C_1$–$C_6$ carboxylic acids selected from the group consisting of alkali metal formates, alkali metal acetates, alkali metal propionates and alkali metal butyrates.

11. The method of claim 1, wherein the one or more polymeric anionic dispersants and salts thereof are selected from homopolymers, copolymers and terpolymers having acid functionalities selected from the group of carboxylic acid, sulphonic acid and phosphonic acid functionalities.

12. The method of claim 1, wherein the one or more polymeric anionic dispersants and salts thereof are selected from homopolymers, copolymers and terpolymers of one or more monomers selected from the group consisting of acrylic acid, methacrylic acid, crotonic acid, maleic acid, maleic anhydride, itaconic acid, mesaconic acid, fumaric acid, citraconic acid, vinylacetic acid, acryloxypropionic acid, vinylsulfonic acid, styrenesulfonic acid, 2-acrylamido-2-methylpropanesulfonic acid, allylsulfonic acid, allylphosphonic acid, vinylphosphonic acid, and vinylsulfonic acid.

13. The method of claim 1, wherein the one or more polymeric anionic dispersants and salts thereof are selected from homopolymers, copolymers and terpolymers of one or more monomers selected from the group consisting of acrylic acid, methacrylic acid, crotonic acid, maleic acid, maleic anhydride, itaconic acid, mesaconic acid, fumaric acid and citraconic acid.

14. The method of claim 1, wherein the one or more polymeric anionic dispersants and salts thereof is a homopolymer of acrylic acid.

15. The method of claim 1, wherein the one or more polymeric anionic dispersants and salts thereof is a homopolymer of acrylic acid prepared using a chain transfer agent.

16. The method of claim 1, wherein the one or more polymeric anionic dispersants and salts thereof is a copolymer of acrylic acid and ethyl acrylate.

17. The method of claim 1, wherein the one or more polymeric anionic dispersants and salts thereof is a copolymer of acrylic acid and ethyl acrylate prepared using a chain transfer agent.

18. The method of claim 1, wherein the one or more polymeric anionic dispersants and salts thereof is a copolymer of acrylic acid and maleic acid.

19. The method of claim 1, wherein the one or more polymeric anionic dispersants and salts thereof is a copolymer of acrylic acid and maleic acid prepared using a chain transfer agent.

20. A stable aqueous slurry of magnesium hydroxide prepared by the method of claim 1.

* * * * *